United States Patent
Al-Salloom

(10) Patent No.: US 10,376,072 B2
(45) Date of Patent: Aug. 13, 2019

(54) PORTABLE LEG CAST SUPPORT

(71) Applicant: Hamad M. A. H. Al-Salloom, Safat (KW)

(72) Inventor: Hamad M. A. H. Al-Salloom, Safat (KW)

( * ) Notice: Subject to any disclaimer, the term of this patent is extended or adjusted under 35 U.S.C. 154(b) by 0 days.

(21) Appl. No.: 16/216,878

(22) Filed: Dec. 11, 2018

(65) Prior Publication Data

US 2019/0183250 A1 Jun. 20, 2019

Related U.S. Application Data

(60) Provisional application No. 62/598,476, filed on Dec. 14, 2017.

(51) Int. Cl.
*A61G 15/00* (2006.01)
*A47C 16/02* (2006.01)
*F16M 11/10* (2006.01)
*F16M 11/28* (2006.01)

(52) U.S. Cl.
CPC ........... *A47C 16/025* (2013.01); *F16M 11/10* (2013.01); *F16M 11/28* (2013.01)

(58) Field of Classification Search
CPC ....... A47C 16/025; A47C 16/02; A47C 16/00; F16M 11/10; F16M 11/28; A61G 15/12; A61G 13/1245; A61G 13/125; A45B 3/00; A61F 5/0585; A61F 5/0195; A61H 3/02; A61H 3/0244; A61M 11/06
See application file for complete search history.

(56) References Cited

U.S. PATENT DOCUMENTS

| | | | | |
|---|---|---|---|---|
| 1,982,388 A | * | 11/1934 | Huehn | A63B 55/57 248/96 |
| 3,415,490 A | * | 12/1968 | Steele | B60S 9/08 254/100 |
| 3,696,826 A | | 10/1972 | Grunzalski | |
| 5,318,068 A | * | 6/1994 | Haugen | A61F 13/041 135/66 |
| 5,735,303 A | * | 4/1998 | Cole | A61H 3/02 135/66 |
| 6,712,781 B1 | | 3/2004 | Sheppard | |
| 9,492,016 B2 | * | 11/2016 | Miller | A61F 5/0195 |
| 2016/0001438 A1 | * | 1/2016 | Buchner | B25H 1/0035 248/647 |
| 2017/0165138 A1 | * | 6/2017 | McCoy | A61G 7/0755 |

* cited by examiner

*Primary Examiner* — Kari K Rodriquez
*Assistant Examiner* — Camtu T Nguyen
(74) *Attorney, Agent, or Firm* — Richard C. Litman

(57) ABSTRACT

A portable leg cast support includes an upper member and a lower member in a telescoping relation. A row of locking holes spanning the length of the upper member allows the telescoping components to be locked together at a user-selectable height for supporting a user's leg cast at an elevated position. A stirrup is pivotally connected to the top of the upper telescopic member for accepting and supporting a leg at the ankle. When the upper and lower telescoping members are in a retracted configuration and the stirrup is folded against the upper member, the support can be strapped to the leg cast for transport until it is needed as a support.

9 Claims, 6 Drawing Sheets

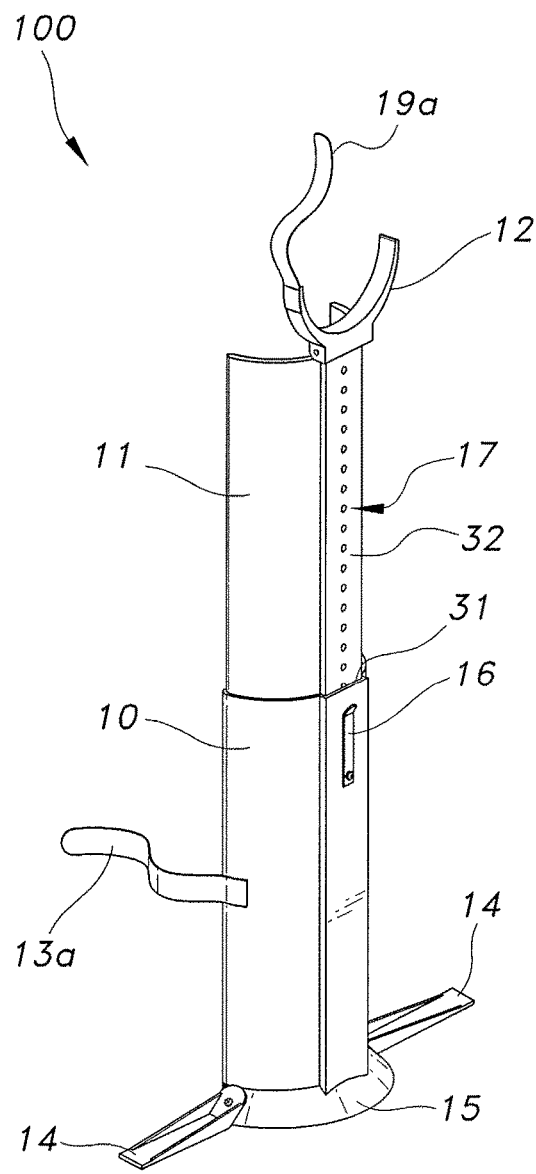
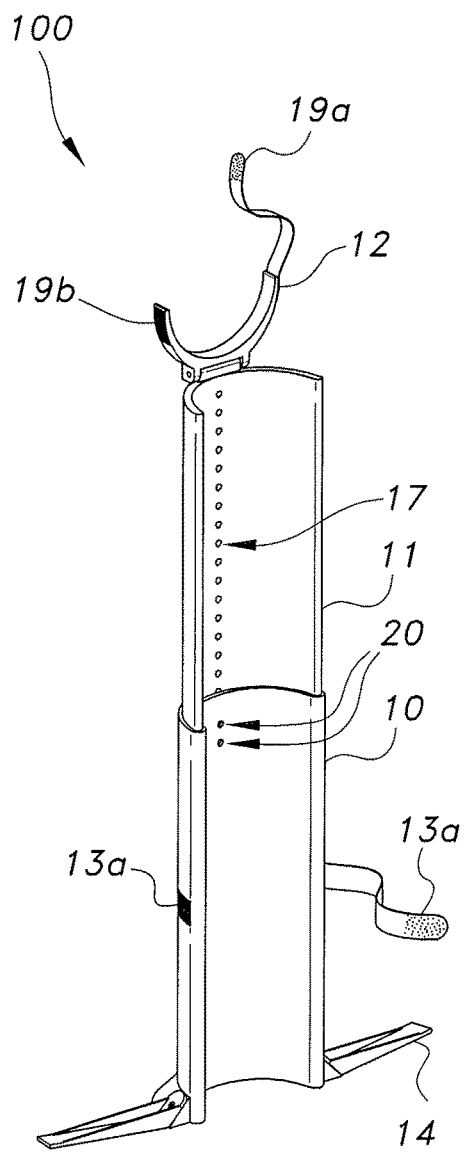
FIG. 1A  FIG. 1B

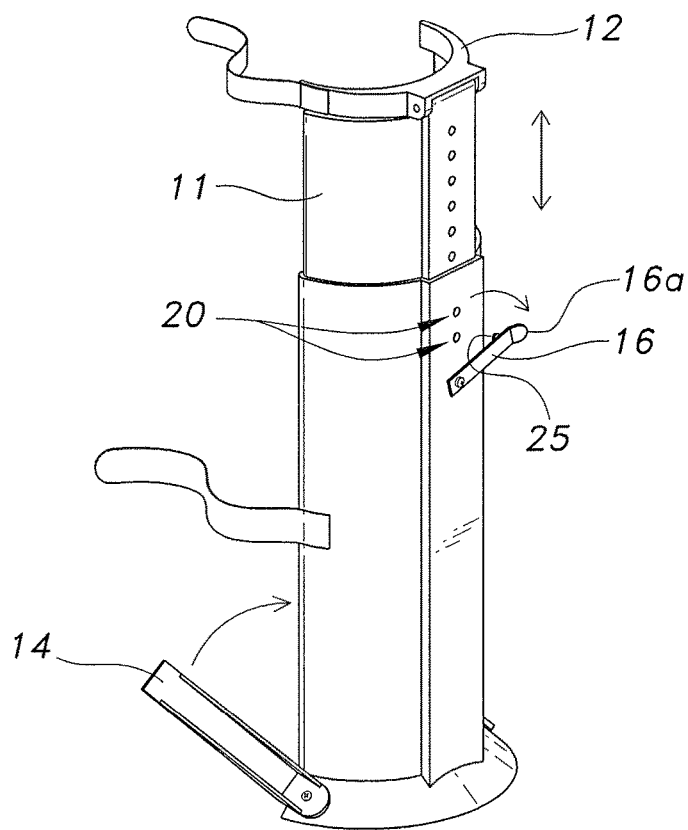
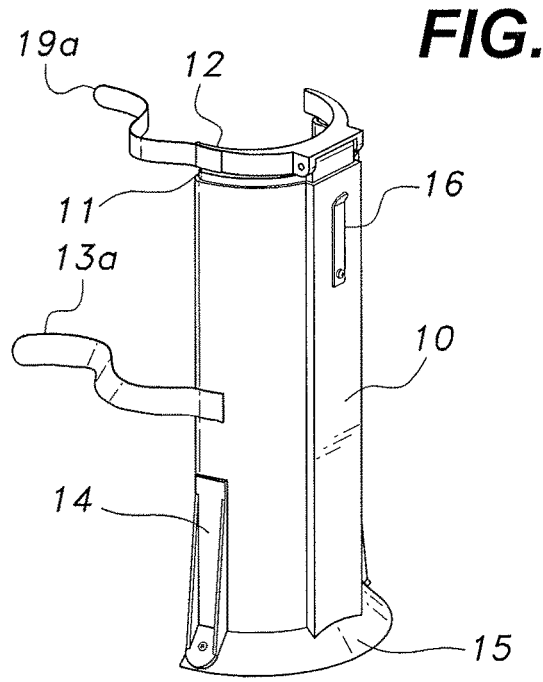
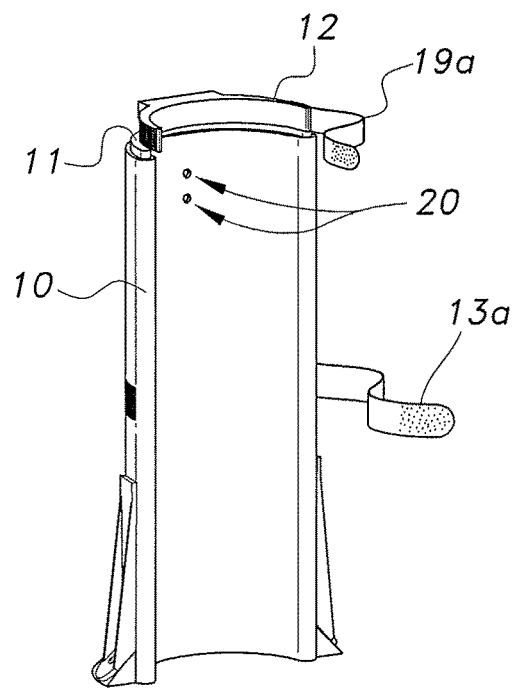
FIG. 2
FIG. 3A                    FIG. 3B

PORTABLE LEG CAST SUPPORT

CROSS-REFERENCE TO RELATED APPLICATION

This application claims the benefit of U.S. Provisional Patent Application Ser. No. 62/598,476, filed Dec. 14, 2017.

FIELD OF THE INVENTION

The disclosure of the present patent application relates to appendage elevation devices to combat swelling, and more particularly to a portable leg cast support capable of telescoping.

DESCRIPTION OF THE RELATED ART

Generally, a person wearing a leg or an arm cast due to an operation, bone breakage or fracture, is required to keep his or her leg or arm in an elevated position. However, it is not always easy to find something to place one's injured leg or arm upon. For example, in a restaurant situation, a person with a cast needs to ask for an extra chair, which, due to lack of space under the table, needs to be placed in an aisle, causing a hassle for the restaurant's employees and embarrassment to the injured person.

Different styles of device have been designed to elevate and support a leg in a cast. However, although elevation of limbs is widely recommended, and even prescribed, for the treatment of various medical conditions, few specialty devices are commonly used. This may be the result of many different factors, such as the cost of these devices, the inconvenience of using and transporting the devices because of their weight and/or bulkiness, or the limited adjustability of the devices.

Thus, a portable leg cast support solving the aforementioned problems is desired.

SUMMARY OF THE INVENTION

The portable leg cast support includes at least an upper member and a lower member in a telescopic relationship. A series of locking holes spanning the length of the upper member allows the telescopic components to be locked together at a user selectable height for supporting a user's leg cast in an elevated position. A stirrup is pivotally connected to the top of the upper telescopic member for attaching the device to the cast at the ankle with an ankle strap, and a leg strap may temporarily secure the telescoping members to the cast. When needed to support the cast, the telescoping members may be pivoted away from the cast at the ankle, and the height may be adjusted for comfort.

These and other features of the present invention will become readily apparent upon further review of the following specification and drawings.

BRIEF DESCRIPTION OF THE DRAWINGS

FIG. 1A is a perspective view of a portable leg cast support in an extended configuration as seen from the rear.

FIG. 1B is a perspective view of the portable leg cast support of FIG. 1A in an extended configuration, as seen from the front.

FIG. 2 is a perspective view of the portable leg cast support of FIG. 1B, shown with the stirrup collapsed against the upper telescopic member.

FIG. 3A is a perspective view of the portable leg cast support of FIG. 1A, shown in a retracted configuration as seen from the rear.

FIG. 3B is a perspective view of the portable leg cast support of FIG. 1A, shown in a retracted configuration as seen from the front.

Similar reference characters denote corresponding features consistently throughout the attached drawings.

DETAILED DESCRIPTION OF THE PREFERRED EMBODIMENTS

The portable leg cast support includes an upper telescopic member and a lower telescopic member in a telescopic relationship. A series of locking holes spanning the length of the upper member allows the telescopic components to be locked together at a user-selectable height for supporting a user's leg cast at an elevated position. When the upper telescopic member and lower telescopic members are in a retracted relationship, the device can be strapped to a user's leg cast for transport until it is needed as a support.

Figures 5A, 5B:
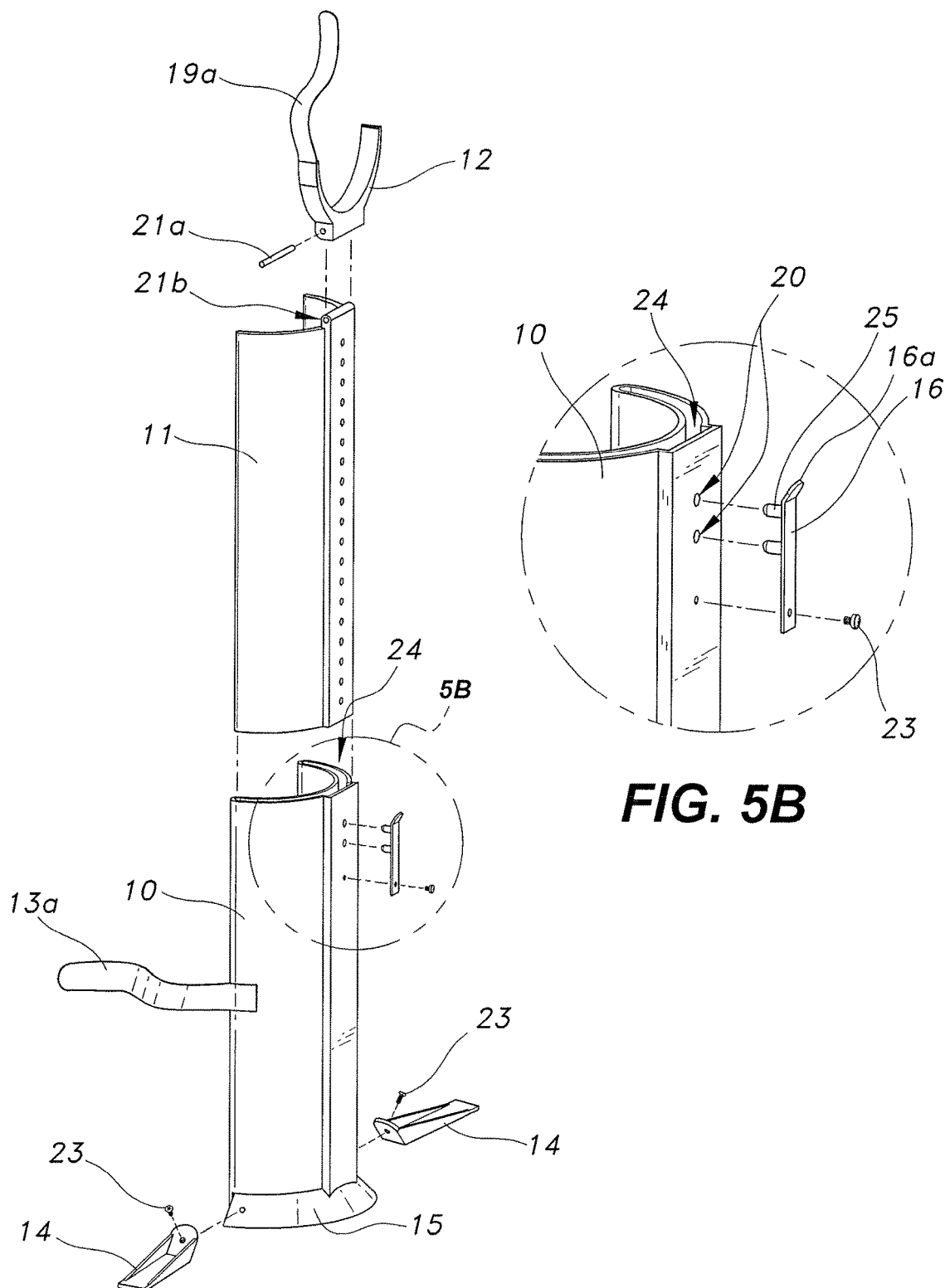
FIG. 5A is an exploded perspective view of the portable leg cast support of FIG. 1A.
FIG. 5B is a partial detail view of area 5B of FIG. 5A.

FIGS. 1A-1B show the support 100 in an extended position for supporting a leg cast at an elevated height. The upper telescopic member 11 is capable of being extended out from the lower telescopic member 10 to raise the height of the support 100. As shown in FIGS. 5A-5B, the relationship between the upper telescopic member 11 and lower telescopic member 10 may be maintained by pins 25 attached to a leaf spring 16 biased against the lower telescopic member 10 that are inserted into aligned holes 20 and locking holes 17 in the upper telescopic member 11. The locking holes 17 may run along the length of the upper telescopic member 11, allowing the height of the support 100 to be adjusted incrementally based on the spacing of the locking holes 17.

Both the upper telescopic member 11 and lower telescopic member 10 may have a semi-circular cross-section. The semi-circular cross section allows the telescopic members 10, 11 to conform to the back of the user's cast, thus providing a low-profile attachment that is not cumbersome when strapped to the user's cast. In addition, the semi-circular cross-section provides rigidity to the telescopic members 10, 11, as well as stability, since it creates a three-dimensional structure and footprint. The lower telescopic member 10 may include a groove 31 running along its length in the center of its rear face. A projection 32 running along the length of the upper telescopic 11 component at the center of its rear face may be dimensioned and configured to match the groove 31 in the lower telescopic component 10 so that the groove 31 acts as a track for the projection 32 to slide in. The interlock between the projection 32 and groove 31 acts to keep the locking holes 17 aligned with the guide holes 20. Additionally, the projection 32 and groove 31 provide extra strength to the portion of the device immediately bearing the weight of the user's leg and cast.

A stirrup 12 is pivotally attached to the upper telescopic member 11 for supporting the user's cast at the ankle. A hinge 21 connecting the stirrup 12 to the upper telescoping member 11 allows the stirrup 12 to pivot from a vertical orientation for supporting a leg cast to a horizontal orientation aligned with the telescopic members for transport. Additionally, the hinge 21 permits the stirrup 12 to align with the angle of the attached cast. The stirrup 12 may have the same semi-circular shape as the telescopic members 10, 11 so that it aligns with the telescopic members 10, 11 when folded down to maintain the low profile of the support 100. The semi-circular shape also acts to cradle the user's cast when being used as a support, and to prevent the leg from unintentionally falling off the support 100. An ankle strap 19a may span the ends of the stirrup 12 to further assist in securing the cast to the support 100. The ankle strap 19a shown in the drawings is securely connected to one end of the stirrup 12 and removably connected at the other end by a hook and loop fastener 19b. Other releasable fastening devices used in the art may be used to secure the strap 19a, including, but not limited to, a buckle or a snap fit connection. The ankle strap 19a may be made of an elastic material.

The bottom 15 of the lower telescopic member 10 may flare out or have an outwardly extending base flange to create a wider base for added stability. When supporting a user's leg, the user's body will provide axial stability, since moving the leg in the axial direction will require the whole body to move. However, the body provides little lateral stability, especially with the added weight of the cast. Therefore, the lower telescoping member 10 may include two stabilizer arms 14 extending out from opposite sides of the bottom 15 in a plane perpendicular to the intended axis of the elevated cast. By increasing the footprint of the support's 100 base in the plane parallel to the axis of the supported cast, the horizontal stability of the support 100 in greatly increased. When in the transport configuration, the stability arms 14 may be folded up, as seen in FIGS. 3A-3B, to decrease the profile of the support 100. Since the flange 15 from which the stability arms 14 extend slopes at 45° relative to the remainder of the lower telescopic component 10, rotating the arms 14 around their point of connection to the flange 15 will align the arms 14 with the body of the lower telescopic member 10.

A leg strap 13a may be connected to the lower telescopic member 10 for securing the device to the user's cast during transportation. The strap 13a may be positioned in the middle of the lower telescopic member 10 and span the open portion of the semi-circle. One end of the strap 13a may be securely connected to the lower telescopic member 10 while the other end of the strap may be removably connected to the opposing side of the lower telescopic member 10 using a hook and loop fastener 14b. Other releasable fastening devices known in the art may be used to secure the strap 13a. These fasteners include, but are not limited to, a buckle or a snap fastener connection. The leg strap 13a may be made from an elastic material.

FIG. 2 shows the adjustability of some of the support's 100 components. The leaf spring 16, which biases the locking pins 25 for height adjustment of the telescopic members 10, 11, may be rotatably connected to the lower telescopic member 10. To adjust the height of the support 100, the locking lever 16 may be rotated away from the guide holes 20 in the lower telescopic member 10. A user unlocks the leaf spring 16 by pulling on the upper tab 16a of the lever to remove the pins 25 from the locking 17 and guide holes 20, and then rotates the locking lever 16 away from the holes 17, 20. Accordingly, the leaf spring 16 may have a resilience that will be flexible enough to allow a user to remove the pins 25 from the holes 17, 20 by hand, while being stiff enough to securely hold the pins 25 in the holes 17, 20 when in use. As previously discussed, the stability arms 14 can be converted to a transport configuration by rotating the arms 14 around their attachment point to align them with the lower telescopic member 10.

FIGS. 3A and 3B show the support 100 in a transport configuration. In the transport configuration, the stirrup 12 is folded down so it is aligned with the telescoping members 10, 11, the telescoping members 10, 11 are retracted to a minimal height, and the stability arms 14 are folded up to align with the telescoping members 10, 11. Both straps 13a, 19a are positioned to wrap around a leg cast placed within the channel created by the semi-circular shape of the telescoping members 10, 11.

Figure 4:
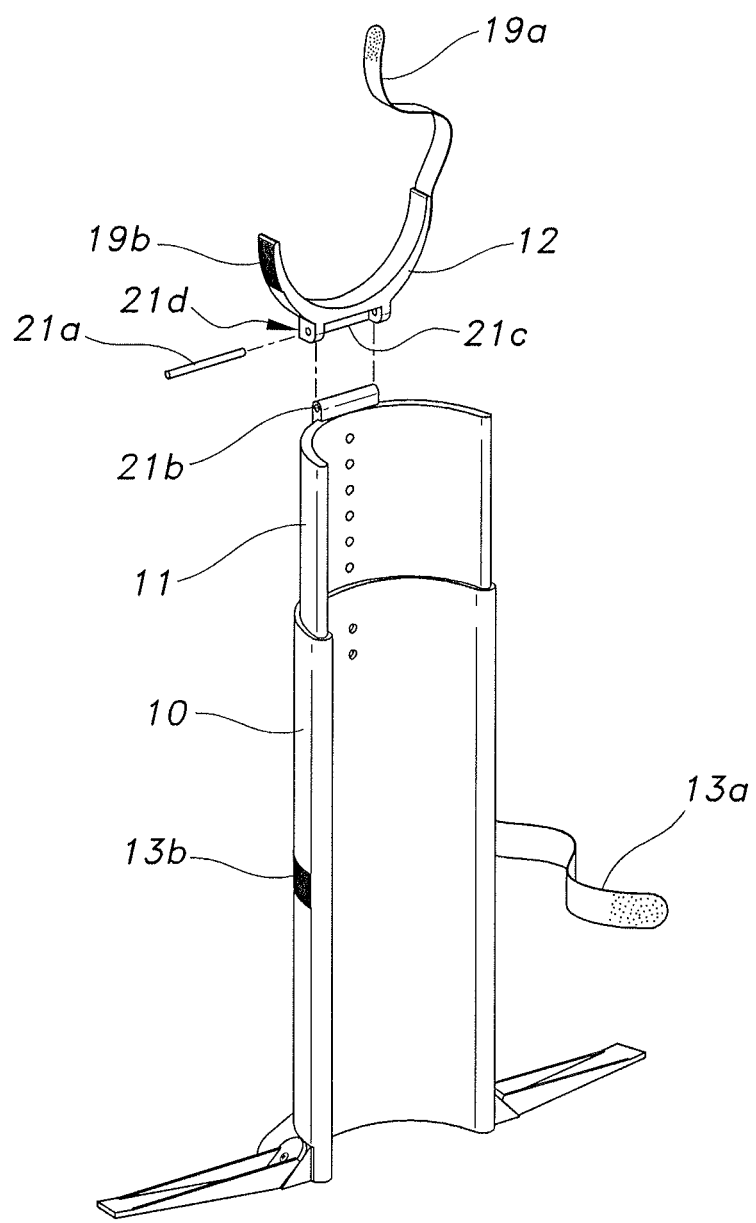
FIG. 4 is a partially exploded perspective view of the portable leg cast support of FIG. 1A, shown with the stirrup hinge exploded.

FIG. 4 details the mechanism that attaches that stirrup 12 to the upper telescopic member 11. The top of the upper telescopic member 11 may include a hinge knuckle 21b. The stirrup 12 may include a slot 21c defined by ears 21d on either side, which is dimensioned and configured to receive the knuckle 21b. A hinge pin 21a extends through the holes in the ears 21d and the bore through the knuckle 21b. Accordingly, the stirrup 12 is able to pivot up and down due to the hinge.

FIG. 5A shows an exploded view of the support 100. The stability arms 14 are secured to the lower telescopic member 10 by screws 23 that thread into the lower telescopic member 10. The threaded connection allows the stability arms 14 to pivot around their respective screws 23 for switching between configurations. The opening 24 at the top of the lower telescopic member 10 is dimensioned and configured to match the cross section of the projection 32 on the upper telescopic member 11, allowing the projection 32 of the upper telescopic member 11 to be inserted into the opening 24, resulting in a freely sliding relationship between the telescopic members 10, 11. When inserted, the matching shapes result in alignment of the locking holes 17 on the upper telescopic member 11 with the guide holes 20 on the lower telescopic members 10.

FIG. 5B details the telescoping members 10, 11 locking mechanism. The leaf spring 16 is attached to the lower telescopic member 10 by a screw 23 that threads into the lower telescopic member 10 immediately below the guide holes 20. The leaf spring 16 includes two pins 25 that extend towards the direction of the lower telescoping member 10, and are positioned to be inserted into the guide holes 20. To lock the telescoping members 10, 11 at a set height, the pins 25 are inserted through the two guide holes 20 in the lower telescoping members 10 and into two locking holes 17 of the upper telescoping member 11 aligned with the guide holes 20. As a result, the upper and lower telescoping members 10, 11 are held in place by the pins 25 and bias applied by the spring 16. To adjust the height of the support 100, a tab 16a at the top of the leaf spring 16 is pulled back to remove the pins 25 from the holes 17, 20, and then the leaf spring 16 is rotated so that the pins 25 are not aligned with the holes 17, 20, allowing the leaf spring 16 to be released. As previously discussed, the leaf spring 16 has a resilience that will be flexible enough allow a user to remove the pins 25 from the holes 17, 20 by hand, while being stiff enough to securely hold the pins 25 in the holes 17, 20 when in use. Stiffness may be adjusted by varying the spring constant of the leaf spring 16.

Figure 6:
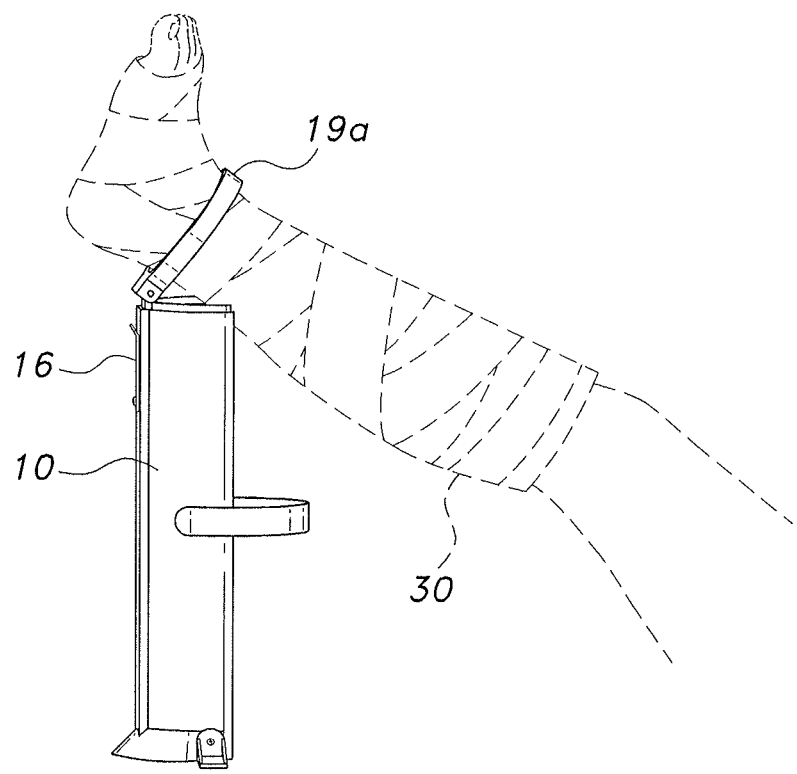
FIG. 6 is an environmental perspective view of a portable leg cast support, shown supporting a cast before height adjustment.
Figure 7:
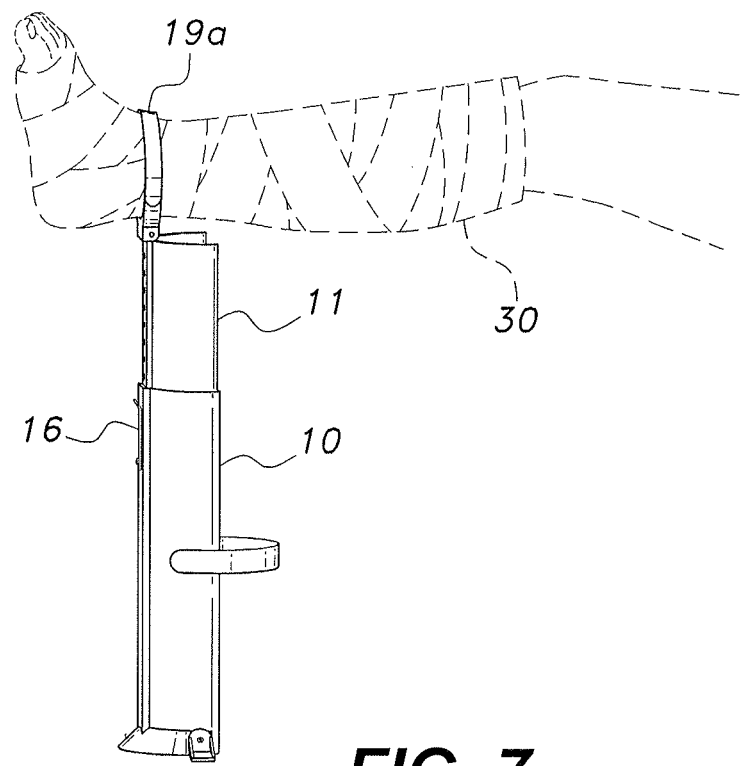
FIG. 7 is an environmental perspective view of a portable leg cast support, shown supporting a cast after height adjustment.

FIGS. 6 and 7 show the device in use as a support 100. In FIG. 6, the user is laying on the ground so that elevation of the leg cast 30 does not require a large support 100 height. Accordingly, the support 100 is set to a minimal height. Since the leg cast 30 is angled upwards, the stirrup 12 tilts back to align with the angle of the leg 30 for providing more stable support. The leg cast 30 is prevented from slipping out of the stirrup 12 by the ankle strap 19a, which extends around the leg cast 30. In FIG. 7, the user is sitting in a chair. In this situation, the support 100 is extended to a greater height to maintain proper elevation. Since the leg 30 is perpendicular to the support 100, the stirrup 12 is in a vertical position to match the leg cast's 30 angle. FIGS. 6 and 7 merely detail example scenarios. The support 100 can accommodate many other height and leg 30 angles. Since the stirrup 12 freely pivots, proper support and securement will be provided from a multitude of leg angles.

Figure 8:
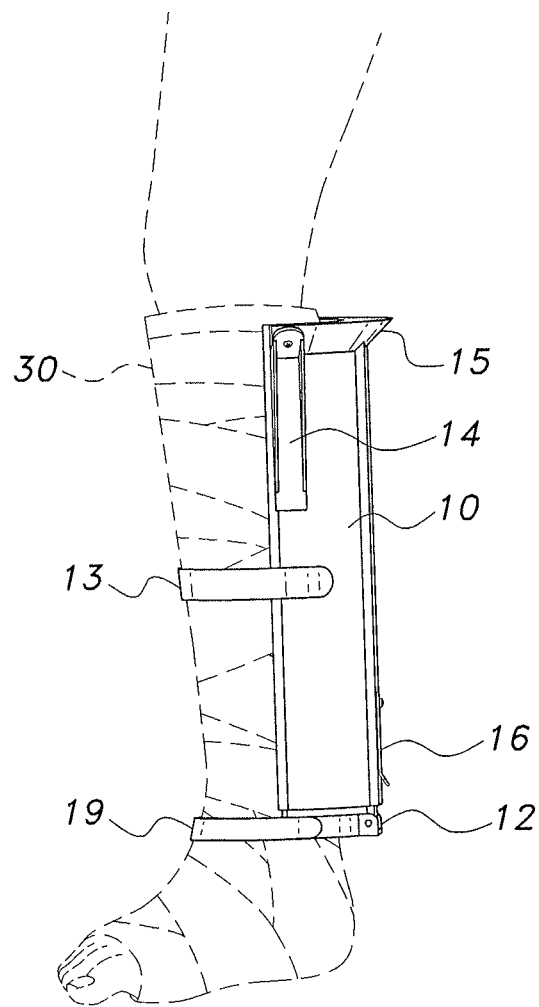
FIG. 8 is an environmental perspective view of a portable leg cast support, shown with the support strapped to the cast for transport.

FIG. 8 shows the support 100 attached to the back of a user's leg cast 30 for transport. The support 100 is set to the transport configuration, where the telescoping members 10, 11 are retracted to a minimal height, the stability arms 14 are aligned with the telescoping members 10, 11, and the stirrup 12 is aligned with the telescoping members 10, 11. The leg strap 13a on the lower telescoping member 10 and the ankle strap 19a on the stirrup 19a both wrap around the cast 30 to securely attach the support 100 to the cast 30. In this configuration, the user can move around as he/she normally would without the support 100 impeding movement.

The support 100 may be made out of any material that has the rigidity and strength to support a casted leg 30. Possible materials include, but are not limited to, steel, aluminum, polyvinylchloride (PVC), and polyethylene. The bottom surface of the lower telescopic member 10, which contacts the ground, may have a high friction coating to prevent slippage and unwanted movement, resulting in a more secure base. Similarly, the cast contacting surface of the stirrup 12 may also have a high friction coating to help prevent the cast from unintentionally sliding out. A compressible pad may also be added to the cast contacting surface of the stirrup 12 to for user comfort. Bearing materials may be added to the inside of the lower telescopic member or the outside of the upper telescopic member to reduce friction and increase durability. An example bearing material is ultra-high-molecular-weight-polyethylene.

The fully extended support 100 may have a height in the range of two to 5 feet. The locking holes 17 may extend along the upper telescoping member 11 for a distance in the range of one to two and a half feet. The distance between the locking holes 17 may be in the range of one-half inch to two inches. The diameter of the semi-circular shape of the telescoping members 10, 11 may be in the range of six inches to a foot. The length of the stabilizer arms 14 may be in the range of two inches to ten inches.

It is to be understood that the portable leg cast support is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

I claim:

1. A portable leg cast support for supporting a patient in a leg cast, comprising:
   an upper member having a top and a lower member, each of the upper and lower members have an arcuate c-shaped cross section configured to receive the leg cast, the upper member and lower member being in a telescoping relationship, the telescoping members being lockable at a user-selectable height, wherein the lower member includes a groove running along its length, the groove subtending a portion of the arcuate cross section of the lower member, the upper member includes a projection running along its length, the projection subtending a portion of the arcuate cross section of the upper member, the projection being dimensioned and configured for sliding in the groove, whereby the groove acts as a track for the projection when the upper member and lower member are in telescoping relation;
   a stirrup pivotally connected to the top of the upper member;
   a releasable ankle strap connected to the stirrup for releasably attaching the stirrup to a leg cast at ankle height; and
   a releasable leg strap connected to the lower member for releasably fastening the telescoping upper and lower members to the leg cast;
   wherein the ankle strap and the leg strap may both be releasably fastened around the leg cast support for transporting the leg cast support attached to the leg cast; and
   wherein the leg strap may be unfastened and the telescoping upper and lower members may be rotated 90° to the stirrup and adjusted in height to bear against a supporting surface to support the leg cast support at ankle height of the leg cast.

2. The portable leg cast support according to claim 1, wherein the stirrup has an arcuate cross-section.

3. The portable leg cast support according to claim 1, wherein the upper member, the lower member, and the stirrup are each arcuate and subtend equal angles.

4. The portable leg cast support according to claim 3, wherein the arcuate stirrup is aligned with the arcuate upper member when pivoted to abut the upper member.

5. The portable leg cast support according to claim 3, wherein the leg strap of the lower member extends across the arcuate lower member and the ankle strap extends across the arcuate stirrup.

6. The portable leg cast support according to claim 1, further comprising a leaf spring pivotally attached to the lower member, the leaf spring having at least one locking pin extending therefrom, the upper member having at least one guide hole defined therein, the telescoping upper member having a row of spaced apart locking holes defined therein, the leaf spring being biased to insert the at least one locking pin through the at least one guide hole and a user selectable one of the locking holes to adjust the height of the telescoping upper and lower members.

7. The portable leg cast support according to claim 6, wherein the projection has a row of locking holes defined therein.

8. The portable leg cast support according to claim 1, wherein the lower member has a base adapted for bearing against a support surface, the support further comprising a first stabilizer arm rotatably attached to the base of the lower member and a second stabilizer arm rotatably attached to the base of the lower member opposite the first stabilizer arm.

9. The portable leg cast support according to claim 8, wherein the stabilizer arms are rotatable from a horizontal position extending transverse to the lower member to a vertical position extending parallel to the lower member.

* * * * *